United States Patent [19]
Biola et al.

[11] 3,980,676
[45] Sept. 14, 1976

[54] METHOD FOR CONTINUOUS PRODUCTION OF PROPYLENE OXIDE

[75] Inventors: Georges Biola, Venissieux; Alain Fabre, Meyzieu; Gerard Schneider, Caluire, all of France

[73] Assignee: Rhone-Poulenc Industries, Paris, France

[22] Filed: Mar. 7, 1975

[21] Appl. No.: 556,406

[30] Foreign Application Priority Data
Mar. 13, 1974 France .............................. 74.09152

[52] U.S. Cl. ........................................ 260/348.5 V
[51] Int. Cl.² ............... C07D 301/06; C07D 301/32

[58] Field of Search ............................. 260/348.5 V

[56] References Cited
UNITED STATES PATENTS
3,238,229  3/1966  Reid .......................... 260/348.5 V

*Primary Examiner*—Norma S. Milestone
*Attorney, Agent, or Firm*—Bacon & Thomas

[57] ABSTRACT

Propylene oxide is continuously produced by oxidation of propylene, and wherein the gaseous products of oxidation are washed with a neutral ester of phosphoric acid to prevent undesirable, competing side reactions.

7 Claims, 1 Drawing Figure

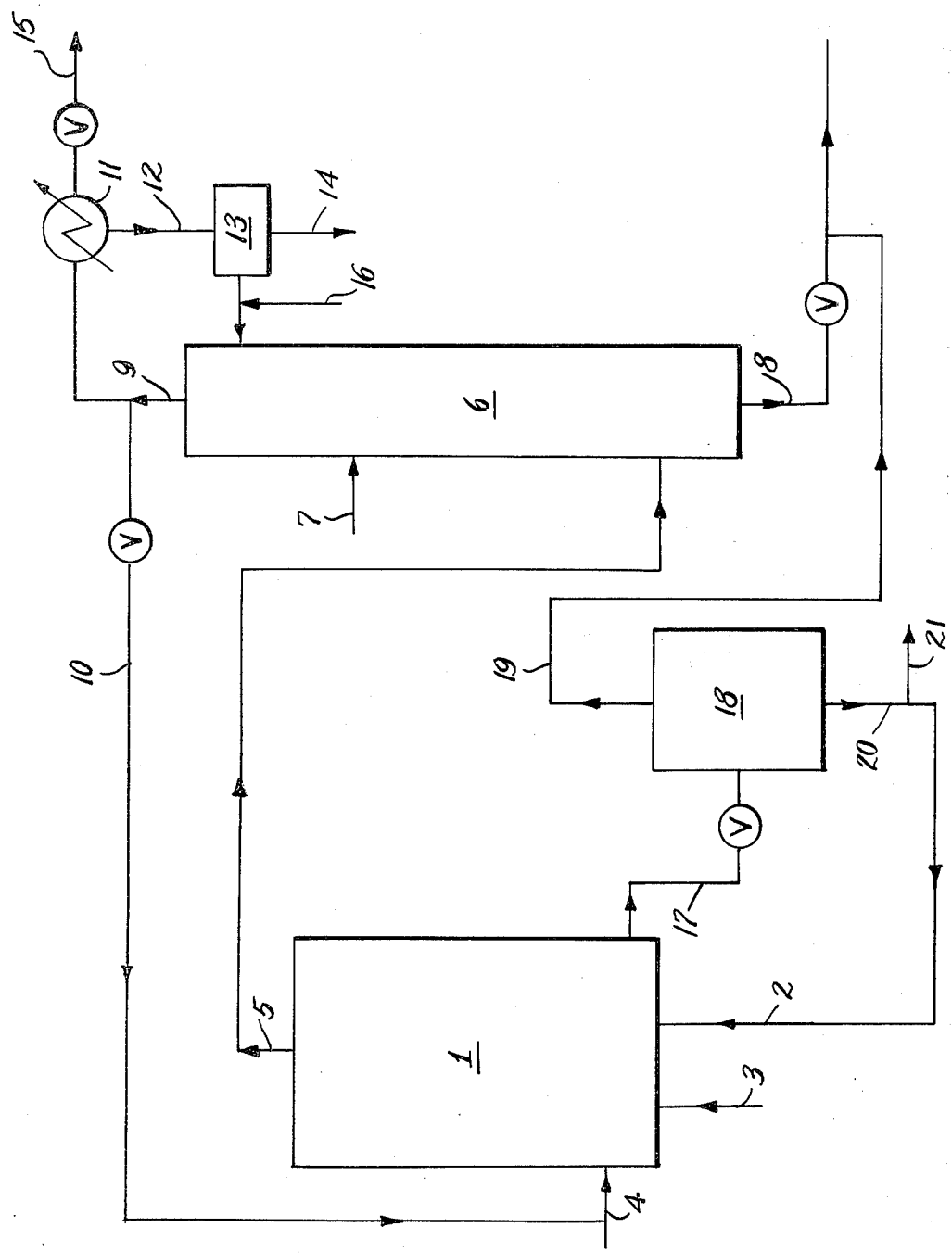

METHOD FOR CONTINUOUS PRODUCTION OF PROPYLENE OXIDE

BACKGROUND OF THE INVENTION

1. Field of the Invention

The present invention relates to a method for the continuous production of propylene oxide by the oxidation of propylene with any one of the conventional oxidizing agents, e.g., air or molecular oxygen.

2. Description of the Prior Art

It is well known in the prior art to prepare propylene oxide by the oxidation of propylene in the liquid phase with air or oxygen. The prior art methods of oxidizing propylene to propylene oxide have certain drawbacks. More particularly, the prior art methods exhibit a low conversion rate of propylene to propylene oxide because of the formation of by-products such as acetic acid and principally formic acid which tend to react with the desired propylene oxide reaction product. Also, the reaction of the aforesaid by-products with propylene oxide gives rise to difficulties in separating the individual constituents of the reaction mixture.

SUMMARY OF THE INVENTION

It has now been surprisingly found that the aforementioned disadvantages of the prior art can be avoided by the utilization of certain additives in the process of this invention which improves the conversion rate of propylene to propylene oxide and further results in a reaction mixture which can be more readily separated.

More particularly according to the invention, there is provided a process for the continuous manufacture of propylene oxide by the oxidation of propylene in liquid phase, under pressure, with molecular oxygen or an oxygen containing gas in a reaction chamber. A gaseous stream is eliminated from the head of such reaction vessel which is washed with a neutral ester of phosphoric acid in a washing vessel to prevent the reaction of acetic acid and formic acid by-products with the desired propylene oxide reaction product. The portion of the gaseous stream which is not extracted by the ester is recirculated into the reaction vessel.

BRIEF DESCRIPTION OF THE DRAWING

The FIGURE of drawing is a diagrammatic representation of the apparatus utilized in the production of propylene oxide according to the present invention.

DETAILED DESCRIPTION OF THE INVENTION

A preferred overall embodiment of the present invention generally involves the oxidation of propylene with molecular oxygen or an oxygen containing gas in the liquid phase and under pressure. During the course of the oxidation of propylene, a gaseous stream is eliminated from the head portion of the reaction vessel which is washed with a neutral ester of phosphoric acid. A liquid current is also withdrawn from the reaction vessel. The said gaseous stream contains vaporized products of the oxidation reaction, more particularly, propylene oxide, organic acids, such as acidic and formic acid, water and other by-products. The gaseous stream also contains oxygen, and inert gases, for example, nitrogen when the oxidizing agent is air, oxides of carbon, propylene and solvent. The gaseous stream is introduced into a washing vessel containing the neutral phosphoric acid ester which absorbs a greater portion of the oxidation products, propylene and solvent. The portion of the gaseous stream not absorbed by the phosphoric acid ester may be treated for the recovery of component products or may be recycled to the reaction chamber.

The washing liquid containing absorbed products of oxidation is withdrawn from the washing vessel and is thereafter treated for the separation of propylene oxide and other useful compounds according to the method disclosed in our copending United States patent application, Ser. No. 546,443, filed Feb. 4, 1975.

Treating the gaseous stream from the head of the reaction vessel with a neutral ester of phosphoric acid prevents the formation of by-products of reactions between the propylene oxide reaction product and the organic acid by-products, such as formic acid and acetic acid. It is supposed that, albeit we do not wish to be bound by such theoretical explanation, the said neutral esters of the phosphoric acid complex with the objectionable acids and hence prevent any such reaction with the propylene oxide product. In addition, the presence of a neutral ester of phosphoric acid facilitates the further separation of propylene oxide as illustrated in the aforementioned copending patent application.

A further embodiment of the invention consists of the recirculation of gases not absorbed by the washing solution, to the reaction vessel. It is supposed that, albeit we again do not wish to be bound by such theoretical explanation, that the recycling of the gases into the reaction vessel produces a stirring of the reaction liquid and the dilution of the oxygen introduced into the reaction chamber, all resulting in a smoother oxidation reaction. This stirring phenomenon and oxygen dilution leads to the improvement of the oxidation selectivity in favor of the formation of propylene oxide. When the said recycled gas is further removed from the reaction vessel to the washing vessel, an increased portion of propylene oxide and organic acid by-products is carried along therewith, thereby reducing the concentration of these compounds in the reaction chamber. Accordingly, by-products due to the reaction of said organic acids with propylene oxide in the reaction chamber are further reduced. Other advantages of the process will become apparent in the following description.

By "neutral ester" of phosphoric acid, there is intended those esters of the following structural formula:

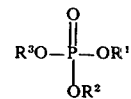

wherein $R^1$, $R^2$ and $R^3$ may be the same or different and are independently selected from the group consisting of lower alkyl having from 1 to 8 carbon atoms, phenyl and alkylphenyl with one to two alkyl groups having from 1 to 3 carbon atoms. Such esters can be employed either alone or in various admixtures, and one readily available commercial product is tri-n-butyl phosphate.

The amount of the phosphoric acid neutral ester which can be employed various over wide limits. In order to determine the lower limit of the phosphoric acid neutral ester to be used, the amount of oxygen introduced to the reaction vessel is taken into account and at least 0.2 moles of ester for each mole of oxygen circulated in the washing column is required. Preferably, an excess of phosphoric acid neutral ester should be utilized, and it should be understood that there is no critical upper limit. The amount of ester utilized in the washing vessel is principally dependent upon the technological requirements of the reaction system. For example, up to ten times the calculated lower limit may be practicable.

The washing procedure itself does not require any particular operating procedure, and would be readily apparent to the skilled worker in the art. The principal caution, however, to be taken into account is to avoid conditions such as would lead to a temperature increase in the washing vessel which would be in excess of the degradation temperature of the neutral phosphoric acid ester. The temperature in the washing vessel may be affected by the temperature of the gaseous stream flowing from the reaction vessel into the washing vessel. If necessary, the aforementioned gases should be suitably cooled before coming into contact with the washing liquid to prevent degradation.

As stated hereinabove, the gases which are not absorbed during the washing step are recirculated to the reaction vessel. The flow rate of the recycled gases must be adjusted so that the pressure in the reaction chamber remains substantially unchanged. Accordingly, a suitable portion of the gas from the washing vessel is not recycled to the reaction vessel, but is treated for the recovery of recycled products.

According to the preferred operating conditions, the temperature in the reaction vessel should be between about 120°C. and 250°C., more preferably between 140°C and 200°C. The reaction may be carried out under a total pressure from about 30 to 100 bars, preferably 40 to 80 bars. The solvent utilized in accordance with this invention should be insoluble in water and substantially immiscible in organic acids, such as formic acid. Examples of said solvents are monochlorobenzene, di(ortho, meta or para) chlorobenzenes, tri(1,2,3-,1,2,4- or 1,3,5-) chlorobenzenes, tetra(1,2,3,4-,1,2,3,5- or 1,2,4,5-) chlorobenzenes. The aforementioned solvents may be used alone or in combination. Known catalysts may also be used, such as napthenates or acetyl-acetonates of molybdenum, tungsten or vanadium.

The liquid which is removed from the bottom portion of the reaction vessel contains principally the solvent of the reaction, unreated propylene and oxidation by-products. This stream from the bottom portion of the reaction vessel may be added to the liquid portion withdrawn from the bottoms of the washing vessel directly. However, it is more advantageous to treat the liquid removed from the bottom portions of the reaction vessel in an expansion device to separate light boiling products. The light boiling products are removed from the head portion of the expansion zone and are added to the stream flowing from the bottoms portion of the washing column. The portion of the liquid not removed from the expansion vessel is solvent which may be recycled to the oxidation vessel.

Referring specifically to the single FIGURE of drawing, to more fully illustrate the various principles of this invention, the oxidation reactor 1 is fed with solvent, propylene and oxygen-containing gas via pipes 2, 3 and 4, respectively. Overhead, a gaseous stream is removed from the reaction vessel and is fed to the bottoms portion of the washing column 6 by line 5. The washing column is fed with phosphoric acid ester by line 7. The washing liquid containing absorbed products is drawn off by pipe 8. Non-absorbed gases leave the head portion of the washing column 6 by line 9. If the said non-absorbed gases are to be recirculated to the reaction vessel, same are fed thereto by line 10 at a suitable flow rate, by utilization of an appropriate device such as, for example, a circulation system for the gas. The feed pipe 10 may directly open into the reactor 1 and according to the most preferred embodiment of the invention, it is preferably connected to the oxygen-containing gas feed pipe 4, thereby resulting in a better dilution of the oxidizing agent. The gaseous fraction not recycled to the reaction vessel 1 is generally a minor portion of the gaseous stream removed from the washing column 6; more specifically when air is used as the oxidation agent, this gaseous fraction equals the flow rate of nitrogen introduced in the reactor 1. The gaseous fraction not recirculated is fed into the condenser 11 where propylene and water formed during the reaction are condensed and are fed by line 12 to decanter 13. The lower phase consisting of water is withdrawn by line 14, while the upper phase consisting of propylene is returned to washing column 6 as a reflux. The inert gases which carry with it a certain proportion of propylene are removed from the condenser 11 by pipe 15 and may be treated for the recovery of propylene. If the non-absorbed gases from washing column 6 are not recycled, the entire gaseous stream escaping from the head portion of column 7 is fed into condenser 11. When the non-absorbed gases from the washing column 6 are recirculated into the reaction zone, propylene may be introduced by line 16, which results in the propylene passing through the head portion of the washing device 6 and is subsequently fed into the reactor 1 by recycling line 10. Accordingly, the reactor may be fed partially or wholly with propylene to be oxidized through line 16. The thermal balance of the washing column and oxidation reactor is accordingly improved.

At the bottoms portion of reactor 1 a liquid fraction of the reaction mixture is fed through line 17. This bottoms fraction is fed to expansion zone 18 where a gaseous phase containing unreacted propylene and oxidation products are separated overhead and are fed through pipe 19 to line 8 containing the liquid flowing from the bottom of washing column 6. The unvaporized solvent in expansion zone 18 is recycled to the oxidation reactor by pipe 20. Heavy products from the expansion zone may be removed through line 21.

In order to more fully illustrate the present invention and advantages thereof, the following specific example is given, it being understood that the same is intended and included as being illustrative only and in no wise limitative.

EXAMPLE

The propylene oxidation was carried out in an apparatus of the type disclosed in the FIGURE of drawing. All parts and percentages are expressed by weight.

The reactor 1, was maintained at a temperature of about 165°C. under a relative pressure of 65 bars and was charged with 172.7 parts per hour of monochlorobenzene via pipe 2 and 55.4 parts per hour of air, via pipe 4, and to which there were added 503.3 parts per hour of recycled gases fed by line 10 and containing 77.2% of propylene.

From the head portion of reactor 1, a gaseous stream of 702.7 parts per hour escaped through pipe 5. This gaseous stream comprised 52.65% propylene, 1.35% propylene oxide, 0.47% formic acid, 0.24% acetic acid and 21.20% of monochlorobenzene. The aforesaid gaseous stream was fed into washing column 6 which was fed by line 7 with 24 parts per hour of tri-n-butyl phosphate. The washing column was maintained at a temperature of 92°C. at the head portion and 130°C. at the bottoms portion. 300 parts per hour of liquid was removed from the bottoms portion of the washing vessel by pipe 8. This liquid contained 70.18% monochlorobenzene, 8% of tri-n-butyl phosphate, 13.72% of propylene and products of the propylene oxidation among which were 3.17% of propylene oxide, 1.09% of formic acid and 0.56% acetic acid. A gaseous stream was removed from the washing column 6 through pipe 9 in a proportion as hereinabove mentioned, and was returned to reactor 1. The remainder of the gas not recycled to reactor 1 was cooled to 20°C. in the condenser 11. The condensed liquid was fed into decanter 13 where, by pipe 14, the lower phase consisting of 0.54 parts per hour of water was withdrawn. The upper phase containing principally propylene was recycled into the column 6. The gases from pipe 15 were washed with monochlorobenzene in a device, not shown, which allowed further recovery of propylene.

140.3 parts per hour of a mixture containing 56.3% of propylene and 43.7% of monochlorobenzene was fed by pipe 16 which consisted of fresh propylene and propylene recovered by washing with monochlorobenzene.

32.2 parts per hour of reaction mixture was removed from the bottoms portion of the reaction vessel 1 in order to maintain a constant level in the reactor. This liquid was fed through pipe 17 to the expansion chamber 18 in two stages, first at 145°C. at 15 bars, then at 135°C. at 1.5 bars. 20.4 parts per hour of the gaseous fraction flowing through line 19 contained as main constituents 20.98% propylene, 2.35% of propylene oxide, 0.52% of formic acid, 0.41% of acetic acid and 70.52% monochlorobenzene. 11.8 parts per hour of a liquid consisting essentially of monochlorobenzene was drawn off from the expansion zone 18 by pipe 20.

While there have been described and pointed out the fundamental novel features of the invention as applied to the preferred embodiments, those skilled in the art will appreciate that various modifications, changes and omissions in method illustrated and described can be made without departing from the spirit of the invention. It is the intention, therefore, to be limited only by the scope of the claims which follow.

We claim:

1. The method for the preparation of propylene oxide, which method comprises oxidizing propylene in liquid phase with molecular oxygen or an oxygen containing gas and thence washing the gaseous stream of said reaction with a neutral ester of phosphoric acid at a temperature below the degradation temperature of said ester whereby a greater portion of the oxidation products, propylene and solvent in said gaseous stream is absorbed by said ester of phosphoric acid.

2. The method as defined by claim 1, further comprising recycling said gaseous products not absorbed by said neutral ester of phosphoric acid to the propylene oxidation zone.

3. The method as defined by claim 3, wherein said gaseous products are recycled to said propylene oxidation zone through an oxygen containing gas stream feeding said oxidation zone.

4. The method as defined by claim 1, wherein the neutral ester of phosphoric acid exhibits the structural formula:

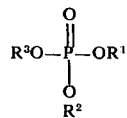

wherein $R^1$, $R^2$ and $R^3$ may be the same or different and are independently selected from the group consisting of lower alkyl having from 1 to 8 carbon atoms, phenyl and phenyl alkyl with one or two alkyl groups having 1 to 3 carbon atoms.

5. The method as defined by claim 4, wherein the neutral ester of phosphoric acid is tri-n-butyl phosphate.

6. The method as defined by claim 1, further comprising feeding propylene at the head of said washing system.

7. The method as defined by claim 1, wherein the solvent of reaction is an aromatic halocarbon.

* * * * *

UNITED STATES PATENT OFFICE
CERTIFICATE OF CORRECTION

PATENT NO. : 3,980,676
DATED : September 14, 1976
INVENTOR(S) : Georges Biola, Alain Fabre and Gerard Schneider It is certified that error appears in the above—identified patent and that said Letters Patent are hereby corrected as shown below:

Column 1, line 61, read "acidic" as -- acetic --.

Signed and Sealed this

Eighteenth Day of January 1977

[SEAL]

Attest:

RUTH C. MASON
Attesting Officer

C. MARSHALL DANN
Commissioner of Patents and Trademarks